US008905910B2

(12) United States Patent
Reichenbach et al.

(10) Patent No.: US 8,905,910 B2
(45) Date of Patent: Dec. 9, 2014

(54) FLUID DELIVERY SYSTEM AND METHOD FOR MONITORING FLUID DELIVERY SYSTEM

(75) Inventors: Stephen H. Reichenbach, Pleasanton, CA (US); George Chao-chih Hsu, San Ramon, CA (US); Yu Fai Law, Daly City, CA (US)

(73) Assignee: Thoratec Corporation, Pleasanton, CA (US)

( * ) Notice: Subject to any disclaimer, the term of this patent is extended or adjusted under 35 U.S.C. 154(b) by 647 days.

(21) Appl. No.: 13/166,771

(22) Filed: Jun. 22, 2011

(65) Prior Publication Data

US 2011/0313238 A1    Dec. 22, 2011

Related U.S. Application Data

(60) Provisional application No. 61/357,439, filed on Jun. 22, 2010.

(51) Int. Cl.
*A61N 1/362* (2006.01)
*A61M 1/10* (2006.01)
*A61M 1/12* (2006.01)

(52) U.S. Cl.
CPC ............. *A61M 1/1086* (2013.01); *A61M 1/122* (2014.02); *A61M 2205/3365* (2013.01)
USPC ........................................................... 600/16

(58) Field of Classification Search
USPC ............................................................. 600/16
See application file for complete search history.

(56) References Cited

U.S. PATENT DOCUMENTS

| 4,957,504 A | 9/1990 | Chardack |
| 5,112,202 A | 5/1992 | Oshima et al. |
| 5,171,212 A | 12/1992 | Buck et al. |
| 5,211,546 A | 5/1993 | Isaacson et al. |
| 5,220,259 A | 6/1993 | Werner et al. |
| 5,289,821 A | 3/1994 | Swartz |
| 5,352,180 A | 10/1994 | Candelon et al. |
| 5,362,206 A | 11/1994 | Westerman et al. |
| 5,370,509 A | 12/1994 | Golding et al. |
| 5,613,935 A | 3/1997 | Jarvik |
| 5,695,471 A | 12/1997 | Wampler |
| 5,711,753 A | 1/1998 | Pacella et al. |

(Continued)

FOREIGN PATENT DOCUMENTS

| CA | 2237203 | 3/1998 |
| EP | 1 354 606 | 10/2003 |

(Continued)

OTHER PUBLICATIONS

International Preliminary Report on Patentability for PCT/US2011/041534, mailed Jan. 10, 2013, 8 pgs.

(Continued)

*Primary Examiner* — Robert N Wieland
(74) *Attorney, Agent, or Firm* — Kilpatrick Townsend and Stockton LLP

(57) ABSTRACT

A fluid delivery system includes an electric motor, a pump driven by the electric motor, and a control system. The control system is programmed to supply a variable voltage to the electric motor, to sense a response of a current of the electric motor to the variable voltage, and to obtain frequency domain information about the response of the current of the electric motor.

30 Claims, 7 Drawing Sheets

(56) References Cited

U.S. PATENT DOCUMENTS

| | | |
|---|---|---|
| 5,725,357 A | 3/1998 | Nakazeki et al. |
| 5,840,070 A | 11/1998 | Wampler |
| 5,888,242 A | 3/1999 | Antaki et al. |
| 5,947,703 A | 9/1999 | Nojiri et al. |
| 6,015,434 A | 1/2000 | Yamane |
| 6,027,498 A | 2/2000 | Mutch et al. |
| 6,066,086 A | 5/2000 | Antaki et al. |
| 6,068,588 A | 5/2000 | Goldowsky |
| 6,071,093 A | 6/2000 | Hart |
| 6,074,180 A | 6/2000 | Khanwilkar et al. |
| 6,080,133 A | 6/2000 | Wampler |
| 6,100,618 A | 8/2000 | Schoeb et al. |
| 6,120,537 A | 9/2000 | Wampler |
| 6,129,660 A | 10/2000 | Nakazeki et al. |
| 6,132,363 A | 10/2000 | Freed et al. |
| 6,135,943 A | 10/2000 | Yu et al. |
| 6,142,752 A | 11/2000 | Akamatsu et al. |
| 6,158,984 A | 12/2000 | Cao et al. |
| 6,162,167 A | 12/2000 | Goldstein et al. |
| 6,176,822 B1 | 1/2001 | Nix et al. |
| 6,183,412 B1 | 2/2001 | Benkowski et al. |
| 6,217,541 B1 | 4/2001 | Yu |
| 6,227,797 B1 | 5/2001 | Watterson et al. |
| 6,234,772 B1 | 5/2001 | Wampler et al. |
| 6,234,998 B1 | 5/2001 | Wampler |
| 6,250,880 B1 | 6/2001 | Woodard et al. |
| 6,264,635 B1 | 7/2001 | Wampler et al. |
| 6,277,078 B1 | 8/2001 | Porat et al. |
| 6,295,877 B1 | 10/2001 | Aboul-Hosn et al. |
| 6,302,661 B1 | 10/2001 | Khanwilkar et al. |
| 6,368,083 B1 | 4/2002 | Wampler |
| 6,394,769 B1 | 5/2002 | Bearnson et al. |
| 6,395,026 B1 | 5/2002 | Aboul-Hosn et al. |
| 6,422,990 B1 | 7/2002 | Prem |
| 6,447,441 B1 | 9/2002 | Yu et al. |
| 6,458,164 B1 | 10/2002 | Weiss |
| 6,532,964 B2 | 3/2003 | Aboul-Hosn et al. |
| 6,547,530 B2 | 4/2003 | Ozaki et al. |
| 6,572,530 B1 | 6/2003 | Araki et al. |
| 6,575,717 B2 | 6/2003 | Ozaki et al. |
| 6,605,032 B2 | 8/2003 | Benkowski et al. |
| 6,623,420 B2 | 9/2003 | Reich et al. |
| 6,634,224 B1 | 10/2003 | Schob et al. |
| 6,640,617 B2 | 11/2003 | Schob et al. |
| 6,688,861 B2 | 2/2004 | Wampler |
| 6,709,240 B1 | 3/2004 | Schmalz et al. |
| 6,709,382 B1 | 3/2004 | Horner |
| 6,711,943 B1 | 3/2004 | Schob |
| 6,716,189 B1 | 4/2004 | Jarvik et al. |
| 6,783,328 B2 | 8/2004 | Lucke et al. |
| 6,808,482 B1 | 10/2004 | Pacella et al. |
| 6,817,836 B2 | 11/2004 | Nose et al. |
| 6,866,625 B1 | 3/2005 | Ayre et al. |
| 6,949,066 B2 | 9/2005 | Bearnson et al. |
| 6,966,748 B2 | 11/2005 | Woodard et al. |
| 6,991,595 B2 | 1/2006 | Burke et al. |
| 7,010,954 B2 | 3/2006 | Siess et al. |
| 7,138,776 B1 | 11/2006 | Gauthier et al. |
| 7,141,943 B2 | 11/2006 | Song et al. |
| 7,150,711 B2 | 12/2006 | Nüsser et al. |
| 7,156,873 B2 | 1/2007 | Nose et al. |
| 7,160,242 B2 | 1/2007 | Yanai |
| 7,160,243 B2 | 1/2007 | Medvedev |
| 7,175,588 B2 | 2/2007 | Morello |
| 7,284,956 B2 | 10/2007 | Nose et al. |
| 7,396,327 B2 | 7/2008 | Morello |
| 7,435,059 B2 | 10/2008 | Smith et al. |
| 7,494,459 B2 | 2/2009 | Anstadt et al. |
| 7,497,116 B2 | 3/2009 | Miyakoshi et al. |
| 7,591,777 B2 | 9/2009 | LaRose |
| 7,645,225 B2 | 1/2010 | Medvedev et al. |
| 7,748,964 B2 | 7/2010 | Yaegashi et al. |
| 7,850,594 B2 | 12/2010 | Sutton et al. |
| 7,861,582 B2 | 1/2011 | Miyakoshi et al. |
| 2001/0009645 A1 | 7/2001 | Noda |
| 2002/0183628 A1 | 12/2002 | Reich et al. |
| 2004/0084398 A1 | 5/2004 | Breitschwerdt et al. |
| 2004/0084399 A1 | 5/2004 | Cook et al. |
| 2004/0152944 A1 | 8/2004 | Medvedev et al. |
| 2004/0215050 A1 | 10/2004 | Morello |
| 2004/0234397 A1 | 11/2004 | Wampler |
| 2005/0159639 A1 | 7/2005 | Skliar et al. |
| 2005/0208095 A1 | 9/2005 | Hunter et al. |
| 2006/0149331 A1 | 7/2006 | Mann et al. |
| 2006/0241335 A1 | 10/2006 | Benkowski et al. |
| 2007/0142923 A1 | 6/2007 | Ayre et al. |
| 2007/0231135 A1 | 10/2007 | Wampler et al. |
| 2007/0282298 A1 | 12/2007 | Mason |
| 2008/0080983 A1 | 4/2008 | Wampler et al. |
| 2008/0085184 A1 | 4/2008 | Wampler et al. |
| 2008/0089779 A1 | 4/2008 | Wampler et al. |
| 2008/0089797 A1 | 4/2008 | Wampler et al. |
| 2008/0183287 A1 | 7/2008 | Ayre |
| 2008/0281146 A1 | 11/2008 | Morello |
| 2009/0005633 A9 | 1/2009 | Schima et al. |
| 2009/0099406 A1 | 4/2009 | Salmonsen et al. |
| 2009/0138080 A1 | 5/2009 | Siess et al. |
| 2009/0156885 A1 | 6/2009 | Morello et al. |
| 2010/0042259 A1 | 2/2010 | Simons |
| 2010/0087742 A1 | 4/2010 | Bishop et al. |
| 2010/0130809 A1 | 5/2010 | Morello |
| 2010/0152526 A1 | 6/2010 | Pacella et al. |
| 2010/0166570 A1 | 7/2010 | Hampton |
| 2010/0185280 A1 | 7/2010 | Ayre et al. |
| 2010/0222632 A1 | 9/2010 | Poirier |
| 2010/0222633 A1 | 9/2010 | Poirier |
| 2010/0222634 A1 | 9/2010 | Poirier |
| 2010/0222635 A1 | 9/2010 | Poirier |
| 2010/0222878 A1 | 9/2010 | Poirier |
| 2011/0032107 A1* | 2/2011 | Sasaki ........................ 340/573.1 |
| 2011/0318203 A1 | 12/2011 | Ozaki et al. |

FOREIGN PATENT DOCUMENTS

| | | |
|---|---|---|
| EP | 1 847 281 A1 | 10/2007 |
| JP | 2002-224066 | 8/2002 |
| JP | 2004-278375 | 10/2004 |
| WO | WO 97/29795 | 8/1997 |
| WO | WO 01/05023 | 1/2001 |
| WO | WO 01/12070 | 2/2001 |
| WO | WO 03/15609 | 2/2003 |
| WO | WO 2004/028593 | 4/2004 |
| WO | WO 2010/101107 | 9/2010 |

OTHER PUBLICATIONS

Ayre et al., "Identifying physiologically significant pumping states in implantable rotary blood pumps using non-invasive system observers", IEEE Engineering in Med. and Biology Soc. vol. 1, pp. 439-442 (2003).

Barletta et al. "Design of a bearingless blood pump", Proceedings from Third Int. Symposium on Magnetic Suspension Technology, Ed. By Nelson J. Groom and Colin P. Britcher, Jul. 1996, pp. I-XIII and 265-274.

Yamazaki et al., Development of a Miniature Intraventricular Axial Flow Blood Pump, ASAIO J., pp. M224-M230 (1993).

* cited by examiner

FLUID DELIVERY SYSTEM AND METHOD FOR MONITORING FLUID DELIVERY SYSTEM

CROSS-REFERENCE TO RELATED APPLICATION

This application claims the benefit of U.S. Provisional Application No. 61/357,439, filed Jun. 22, 2010, which is incorporated herein by reference.

FIELD OF THE INVENTION

The present invention relates to a fluid delivery system and a method for monitoring a fluid delivery system, in particular a ventricular assist device. The present invention relates also to a method for computing the flow rate of a pump. The present invention relates further to a computer readable storage medium.

BACKGROUND OF THE INVENTION

Fluid delivery systems are widely used. An example of a fluid delivery system is a blood pump system. The human heart can become damaged or dysfunctional over time. When damage to the heart becomes sufficiently serious, the heart fails to pump and circulate blood normally, resulting in a condition known as heart failure. Around the world millions of people suffer from heart failure. Many people are unresponsive to pharmacological intervention and could benefit from a heart transplant. However, there is a shortage of donor hearts. As a result, implantable blood pumps have gradually evolved into a viable treatment option.

In a diseased state, one or both of the ventricles of the heart can become greatly weakened to an extent that mechanical intervention is needed to keep a patient alive. In extreme circumstances, the entire heart is removed and replaced with an artificial heart while in other cases a heart assist device is used. A blood pump system used without removing the natural heart is commonly referred to as a ventricular assist device.

Although either of the ventricles of the heart may function in a weakened state, failure of the left ventricle is more common. Normally, blood enters the left ventricle through the mitral valve and, during heart systole, the blood is ejected through the aortic valve and into the aorta by the squeezing action of the left ventricle. To assist a failing left ventricle, an implantable ventricular assist device can be attached to the apex of the left ventricle supplementing blood flow between the left ventricle and the aorta. As a result, blood entering the left ventricle may either be ejected through the aortic valve by the ventricle or pass through the ventricular assist device and into the aorta.

Ventricular assistance has been performed by a variety of blood pump designs. The majority of the early ventricular assist devices, such as positive displacement pumps, pumped blood in a pulsatile manner. In this case, the ventricular assist device has allows an internal sac to passively fill with blood and then utilizes pneumatic action to compress the internal sac, ejecting the blood into the patient's aorta to supplement circulation. These pulsatile ventricular assist devices are large and can only be used as an implantable treatment option for patients with a large body surface area.

To overcome the size and reliability problems associated with the pulsatile ventricular assist devices, designers have begun to use continuous flow pumps. These pumps are smaller than their pulsatile counterparts and are more reliable. Continuous flow pumps are normally either centrifugal flow pumps or axial flow pumps. In the centrifugal flow pumps, the rotors are shaped to accelerate the blood circumferentially and thereby cause it to move toward the outer rim of the pump, whereas in the axial flow pumps the rotors are cylindrical with helical blades, causing the blood to be transported in the direction of the rotor's rotational axis.

One problem that can occur with a blood pump is that thrombus forms in the pump or is ingested, causing pump occlusion. Pump occlusion can create a number of problems. For example, pump occlusion can restrict blood flow through the pump, causing blood flow errors and disruptive blood flow conditions. Furthermore, pump occlusion causes resistive forces that reduce the pump system's overall efficiency.

One complicating factor in troubleshooting pump occlusion is that a patient's physiological conditions can also increase pump pressure and reduce pump flow. Such physiological conditions may include, for example, a restriction of the patient's peripheral vascular system. To differentiate between pump occlusion and patient's physiological conditions may be difficult and often requires the use of echocardiography. In addition, sensors, such as flow meters and pressure transducers, have been incorporated into blood pumps to help differentiate the different conditions and monitor the system. However, flow meters and pressure transducers add to the complexity, size and cost of the blood pump system, and also add complexity to the surgical procedure for implanting the blood pump system. In addition, flow meters and pressure transducers could be encapsulated or coated with biological materials and tissues can grow onto the sensing surfaces, rendering the flow meters and pressure transducers unfit for long-term use.

Another problem associated with pump thrombus is that it makes estimating pump flow rate more difficult and less accurate. Methods for estimating the flow rate of a blood pump without the use of a flow meter or pressure transducer have been suggested. For example, the parameters of an electric motor that drives a blood pump can be used to estimate the flow rate of the blood pump. However, these methods are not reliable when thrombus forms in a blood pump.

In summary, available methods for monitoring pump occlusion are complex, large, costly, and in some cases unreliable.

SUMMARY OF THE INVENTION

The present application discloses a method for monitoring system performance, which can differentiate the effects of other physiological conditions. This method does not require the use of flow meters or pressure transducers. In fact, the method may not require any additional hardware to be added to the pump system. This allows the method to be easily and inexpensively implemented in new blood pump systems and to be readily retrofitted in existing blood pump systems, without compromising the systems' performance, reliability, and usability.

Aspects of the present invention are directed to a system configured to control, monitor, or evaluate a blood pump driven by a motor. The system comprises a device programmed to analyze a driving signal with a non-steady component to the motor or the blood pump and a corresponding response signal received from the motor or to analyze two different response signals received from the motor resulting from the driving signal with the non-steady component, and to determine from the analysis whether the blood pump is in operation under either a pump event or a physiological event.

In aspects directed to the system, the analysis includes generating information including one or a combination of frequency domain information, time domain information, and amplitude information, and comparing the information with data representative of one or both of the pump event and the physiological event.

In aspects directed to the system, the system includes a memory device storing data representative of one or both of the pump event and the physiological event, the memory device in communication with the device programmed to analyze.

In aspects directed to the system, the pump event is one or a combination of events selected from the group consisting of occlusion, additional friction within the blood pump, thrombosis within the blood pump, kink in a graft or artificial conduit attached to the blood pump, increased drag on a rotor of the blood pump, increased drag on an impeller of the blood pump, and increased drag on an internal bearing of the blood pump.

In aspects directed to the system, the physiological event is a change in peripheral vascular resistance.

In aspects directed to the system, the physiological event is a condition selected from the group consisting of hypertension, hypotension, hypervolemia, tachycardia, arrhythmia, and tamponade.

In aspects directed to the system, the device is programmed to match, in accordance with the analysis, an operating condition of the blood pump to a specific pump event from a plurality of pump events including occlusion, additional friction within the blood pump, thrombosis within the blood pump, kink in a graft or artificial conduit attached to the blood pump, increased drag on a rotor of the blood pump, increased drag on an impeller of the blood pump, increased drag on an internal bearing of the blood pump, and combinations thereof. In further aspects, the analysis includes phase-and-power analysis, amplitude-and-power analysis, or a combination thereof.

In aspects directed to the system, the device is programmed to distinguish, in accordance with the analysis, the specific pump event from any one or plurality of physiological events including hypertension, hypotension, hypervolemia, tachycardia, arrhythmia, and tamponade. In further aspects, the analysis includes one or a combination of phase-and-power analysis, amplitude-and-power analysis, peak amplitude frequency analysis, frequency-domain analysis, time-domain analysis, and time-frequency-domain analysis.

In aspects directed to the system, the driving signal is based on the heart of a patient.

In aspects directed to the system, the device is configured to supply the driving signal to the motor.

In aspects directed to the system, the analysis includes generating frequency domain information that includes one or more of a transfer function component of the driving signal to the response signal, and a transfer function component of a first signal of the two different response signals to a second signal of the two different response signals, wherein each of the transfer function components includes phase information or amplitude information.

In aspects directed to the system, the analysis includes generating frequency domain information that includes a transfer function of a pair of signals, the pair of signals selected from the group consisting of motor voltage and motor current, motor voltage and rotor speed, motor voltage and motor power, speed command signal and motor current, speed command signal and rotor speed, speed command signal and motor power, motor current and rotor speed, and motor power and rotor speed. In further aspects, the transfer function component is amplitude information of a first signal of the pair of signals at a selected frequency divided by amplitude information of a second signal of the pair of signals at the selected frequency. In further aspects, the device is programmed to determine a degree of pump occlusion based at least on the transfer function.

In aspects directed to the system, the analysis includes generating frequency domain information that includes a phase angle of the response signal at a selected frequency. In further aspects, the frequency domain information includes a phase difference, the phase difference being a phase angle of the driving signal at the selected frequency minus a phase angle of the response signal at the given frequency. In further aspects, the device is programmed to determine a degree of pump occlusion based at least on the phase difference.

In aspects directed to the system, the device is programmed to determine a degree of pump occlusion based at least on one or more of: (a) a phase difference between the driving signal and the response signal at a selected frequency, (b) a predetermined relationship between a degree of pump occlusion and a phase difference between the driving signal and the response signal, (c) whether a phase difference between the driving signal and the response signal is negative or positive, (d) a historic record of phase difference between the driving signal and the response signal, and (e) a change in a phase difference between the driving signal and the response signal has decreased.

Aspects of the present invention are directed to a pump system functioning as a ventricular assist device. The pump system comprises a blood pump and a device according to any one or any combination of the above aspects directed to the system.

Aspects of the present invention are directed to a method of monitoring for controlling a blood pump driven by a motor. The method comprises analyzing a driving signal with a non-steady component to the motor or the blood pump and a corresponding response signal received from the motor, or analyzing two different response signals received from the motor resulting from the driving signal with the non-steady component, and determining from the analysis whether the blood pump is in operation under either a pump event or a physiological event.

In aspects directed to the method, the analyzing step includes generating information including one or a combination of frequency domain information and time domain information, and comparing the information with data representative of one or both of the pump event and the physiological event.

In aspects directed to the method, the pump event is selected from the group consisting of occlusion, additional friction, thrombosis, kink in a graft or artificial conduit attached to the blood pump, increased drag on a rotor of the blood pump, increased drag on an impeller of the blood pump, increased drag on an internal bearing of the blood pump, and combinations thereof.

In aspects directed to the method, the physiological event is a change in peripheral vascular resistance.

In aspects directed to the method, the physiological event is selected from the group consisting of hypertension, hypotension, hypervolemia, tachycardia, arrhythmia, and tamponade.

In aspects directed to the method, the determining step includes matching an operating condition of the blood pump to a specific pump event from a plurality of pump events including occlusion, additional friction, thrombosis, kink in a graft or artificial conduit attached to the blood pump, increased drag on a rotor of the blood pump, increased drag on an impeller of the blood pump, increased drag on an internal bearing of the blood pump, and combinations thereof.

In aspects directed to the method, the analysis step includes phase-and-power analysis, amplitude-and-power analysis, or a combination thereof.

In aspects directed to the method, the determining step includes distinguishing the specific pump event from at least one physiological event including hypertension, hypotension, hypervolemia, tachycardia, arrhythmia, and tamponade.

In aspects directed to the method, the analysis step includes phase-and-power analysis, amplitude-and-power analysis, peak amplitude frequency analysis, frequency-domain analysis, time-domain analysis, time-frequency-domain analysis, and any combination thereof.

In aspects directed to the method, the driving sign is based on the heart of a patient.

In aspects directed to the method, the method includes supplying the driving signal to the motor.

In aspects directed to the method, the analyzing step includes generating frequency domain information that includes one or more of a transfer function of the driving signal to the response signal, and a transfer function of a first signal of the two different response signals to a second signal of the two different response signals.

In aspects directed to the method, the analyzing step includes generating frequency domain information that includes a transfer function of a pair of signals, the pair of signals selected from the group consisting of motor voltage and motor current, motor voltage and rotor speed, motor voltage and motor power, speed command signal and motor current, speed command signal and rotor speed, speed command signal and motor power, motor current and rotor speed, and motor power and rotor speed. In further aspects, the transfer function is an amplitude of a first signal of the pair of signals at a selected frequency divided by an amplitude of a second signal of the pair of signals at the selected frequency.

In aspects directed to the method, the device is programmed to determine a degree of pump occlusion based at least on the transfer function.

In aspects directed to the method, the analysis step includes generating frequency domain information that includes a phase angle of the response signal at a selected frequency. In further aspects, the frequency domain information includes a phase difference, the phase difference being a phase angle of the driving signal at the selected frequency minus a the phase angle of the response signal at the given frequency.

In aspects directed to the method, the method includes determine a degree of pump occlusion based at least on the phase difference.

In aspects directed to the method, the method includes determining a degree of pump occlusion based at least on one or more of: (a) a phase difference between the driving signal and the response signal at a selected frequency, (b) a predetermined relationship between a degree of pump occlusion and a phase difference between the driving signal and the response signal, (c) whether a phase difference between the driving signal and the response signal is negative or positive, (d) a historic record of phase difference between the driving signal and the response signal, and (e) a change in a phase difference between the driving signal and the response signal.

Aspects of the present invention are directed to a computer-readable storage medium, with instructions thereon that are executable by a computer to analyze a driving signal with a non-steady component to the motor or the blood pump and a corresponding response signal received from the motor, or to analyze two different response signals received from the motor resulting from the driving signal with the non-steady component, and to determine from the analysis whether the blood pump is in operation under either a pump event or a physiological event.

In aspects directed to the computer-readable storage medium, the instructions include instructions to generate information including one or a combination of frequency domain information and time domain information, and comparing the information with data representative of one or both of the pump event and the physiological event.

In aspects directed to the computer-readable storage medium, pump event is a condition selected from the group consisting of occlusion, additional friction within the blood pump, thrombosis within the blood pump, kink in a graft or artificial conduit attached to the blood pump, increased drag on a rotor of the blood pump, increased drag on an impeller of the blood pump, increased drag on an internal bearing of the blood pump, and combinations thereof.

In aspects directed to the computer-readable storage medium, the physiological event is a change in peripheral vascular resistance.

In aspects directed to the computer-readable storage medium, the physiological event is a condition selected from the group consisting of hypertension, hypotension, hypervolemia, tachycardia, arrhythmia, and tamponade.

In aspects directed to the computer-readable storage medium, the instructions include instructions to match an operating condition of the blood pump to a specific pump event from a plurality of pump events including occlusion, additional friction within the blood pump, thrombosis within the blood pump, kink in a graft or artificial conduit attached to the blood pump, increased drag on a rotor of the blood pump, increased drag on an impeller of the blood pump, increased drag on an internal bearing of the blood pump, and combinations thereof. In further aspects, the instructions include instructions to perform phase-and-power analysis, amplitude-and-power analysis, or a combination thereof.

In aspects directed to the computer-readable storage medium, the instructions include instructions to distinguish the specific pump event from a plurality of physiological events including hypertension, hypotension, hypervolemia, tachycardia, arrhythmia, and tamponade. In further aspects, the instructions include instructions to perform one or a combination of phase-and-power analysis, amplitude-and-power analysis, peak amplitude frequency analysis, frequency-domain analysis, time-domain analysis, and time-frequency-domain analysis. In aspects directed to the computer-readable storage medium, the instructions include instructions to determine a degree of pump occlusion based on one or more of: (a) a phase difference between the driving signal and the response signal at a selected frequency, (b) a predetermined relationship between a degree of pump occlusion and a phase difference between the driving signal and the response signal, (c) whether a phase difference between the driving signal and the response signal is negative or positive, (d) a historic record of phase difference between the driving signal and the response signal, and (e) a change in a phase difference between the driving signal and the response signal.

DETAILED DESCRIPTION OF PREFERRED EMBODIMENTS

Figure 1:
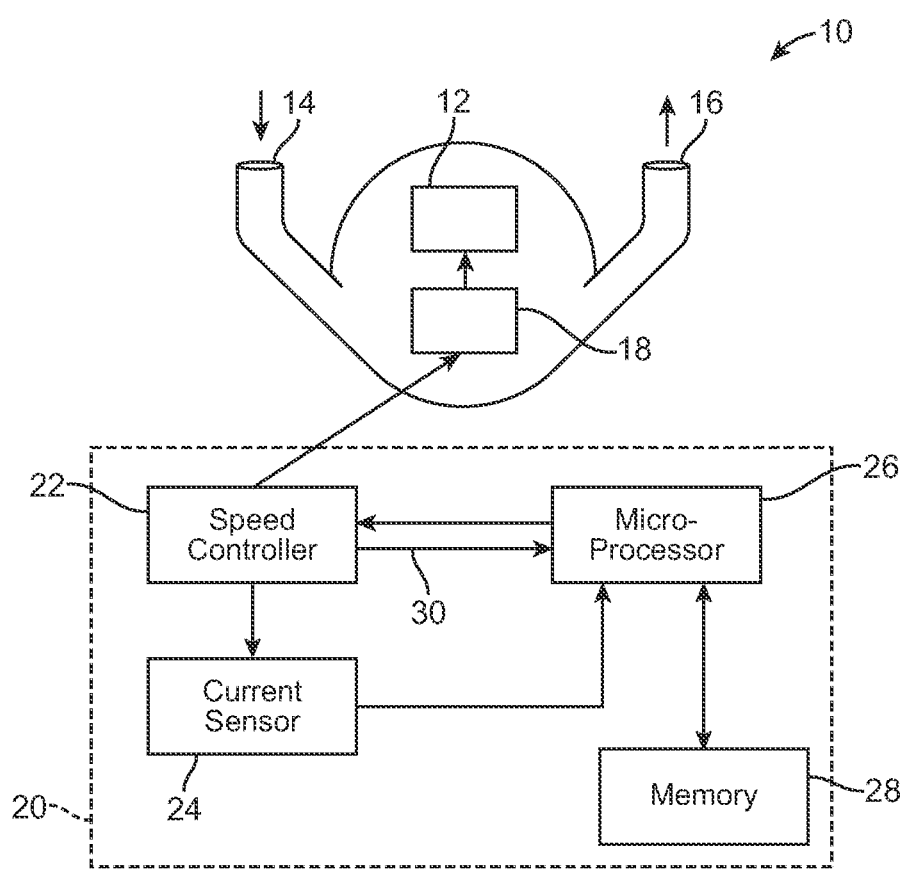
FIG. 1 is a schematic drawing of a ventricular assist device according to the present invention.

FIG. 1 shows a schematic diagram of a ventricular assist device 10 according to a preferred embodiment of the present invention. Although the ventricular assist device 10 is used to illustrate the present invention, the invention can be used with any suitable fluid delivery system. The device 10 includes an implantable pump 12 that can be connected to a patient's circulatory system. The pump 12 has an inlet 14 and an outlet 16. The pump can be an axial flow pump, a centrifugal pump, a positive displacement pump, or any other type of blood pump. The inlet 14 may connect to a conduit (not shown) that may in turn connect to a patient's circulatory system, such as at the left ventricle of the patient's heart. The outlet 16 may connect to another conduit (not shown) that may in turn connect to the patient's circulatory system downstream of the first conduit, such as in the aorta. The pump 12 can be implanted in the patient's abdomen, chest cavity, or in another location.

The ventricular assist device 10 also includes an electric motor 18 for driving the pump 12. The electric motor 18 can be of any suitable type. For example, the electric motor 18 can be an alternating current electric motor or a direct current electric motor. The electric motor 18 could be a continuous type electric motor or a stepper type electric motor. The electric motor 18 and pump 12 may form an integral unit or separate units. The electric motor can be integrated into the pump such that the motor rotor is the same as the pump rotor.

The ventricular assist device 10 also includes a control system 20 that can be located inside or outside the pump 12. The control system 20 can be configured to operate the pump 12 (or the electric motor 18) at a particular speed or speeds to provide adequate assistance to the patient's heart. The control system 20 can adjust the speed of the electric motor 18 by means of a speed controller 22 of the control system 20.

The control system 20 can include a microprocessor 26 that is used to control the electric motor 18 to establish and control an appropriate set point for the pump 12. The control system 20 can also include a current sensor 24 that senses the current drawn by the electric motor 18, and the microprocessor 26 can use the current signal to compute the flow rate of the pump 12.

In addition, the microprocessor 26 can receive a signal on a speed line 30 that indicates the rotational speed of the electric motor 18 (or the pump 12). The speed of the electric motor 18 can be measured from the electric motor's back electromotive force signal. The control system 20 can further include memory 28 for storing data.

In the above described ventricular assist device 10, thrombus may form over time in the pump 12, causing pump events such as occlusion, additional friction, or combination of the two. Because of the many problems that pump events may cause, it is desirable to detect pump occlusion when it occurs. But, it is commonly believed that, as discussed above, it is difficult to accurately determine the existence of pump events without the use of flow and pressure sensors or echocardiography. One reason for the difficulty is that, without the use of sensors or echocardiography, the current methods cannot differentiate the effects of pump events on a fluid delivery system from the effects of a patient's physiological conditions.

This disclosure focuses on two main goals of detecting adverse pump events. First, the invention identifies the existence of occlusion, additional friction, and/or thrombosis (combination of occlusion and additional friction). The methods of identification include phase-and-power analysis techniques, amplitude-and-power analysis techniques, and any combination or variation of the forgoing techniques. The second focus of the invention is the ability to differentiate between the effect of pump events and the effect arising from the patients' physiological conditions. The methods for differentiation include phase-and-power analysis techniques, amplitude-and-power analysis techniques, peak amplitude frequency analysis techniques, frequency-domain analysis techniques, time-domain analysis techniques, time-frequency-domain analysis techniques, and any combination or variation of the forgoing techniques. The mathematical analysis techniques listed above are employed to circumvent the need for additional sensors. In the following discussion of the signal analyses, the control system performs analysis on the relative difference or ratio of two different pump parameters (signals). Various combinations of parameters or signals that can be analyzed include without limitation: variable voltage and motor current, variable voltage and rotor speed, variable voltage and motor power, variable speed command and motor current, variable speed command and rotor speed, variable speed command and motor power, the motor current and the rotor speed, the motor power and the rotor speed. In each example described below, one of these parameter combinations may be mentioned though it should be understood that another one of the parameter combinations may also be used. Therefore, it is possible to analyze a driving signal and a response signal together or to analyze two different response signals together for the purpose of differentiating effects between pump events and physiological conditions.

In regard to the focus of the invention (detecting adverse pump events), one method of overcoming the lack of sensors is to have the control system apply mathematical analysis to interpret pump (motor) response signals obtained from a pump representing the pump's response to an injected disturbance which can come from the natural heart and/or can be artificially generated and supplied by the control system.

For example, the natural heart beat coming from the heart is one form of natural disturbance. Each heart beat creates a pressure pulse that results in a variation in the differential pressure of the pump. This differential pressure is seen by the pump as a variation in load, which directly causes a change in speed and/or voltage. Hence, a natural disturbance can result in a non-steady input to the system. The injected disturbance can be non-steady state speed or voltage waveforms such as sinusoidal, chirp, step, pulse, etc. that is artificially created and imposed on the system. The pump (motor) response signals are captured in form of speed, current, and/or power. While motor voltage and current can be directly measured and the power determined at the controller, speed of the pump rotor is measured from the motor's back EMF signal. One or any combination of these various response signals can be collected in real time as the pump is driven by the sinusoid superimposed voltage for any short periods of time.

The sinusoidal driving signal causes response signals (e.g., speed and current) to vary about their normal values. To assess and control the pump, the following are used: the average power and phasic relation between the pump's driving and response signals, and/or the average power and phasic relation between functions of the response signals such as computed power. Furthermore, an algorithm can replace the phasic information with the transfer function in the analysis to assess and control the system. Additional analysis methods that incorporate wide range of frequencies in the frequency domain or both the frequency and time domain information are used in combination with the basic Fourier Transform analysis to assess the system.

For instance, a pump such as a VAD (ventricular assist device) connected to the circulation system with an unobstructed connection to the heart and aorta can have a speed signal wave that leads the voltage wave. Consequently, the signals have a particular phase relationship (e.g., where difference of phase angles of voltage and speed is negative). When an event occurs like an occlusion or stenosis occurring at the pump or conduits, the phase angle relationship changes.

Troubleshooting or identification of different conditions can be performed using variants of the above technique. For example, impingement on the pump rotor (i.e., increase in drag on rotor/impeller) results in an increase of pump power as well as over prediction by a flow estimator. The phase shift arising from pump impingement on the pump rotor would be different from that arising from a high flow condition which causes an increase in power under normal circumstances. When flow is decreased beyond the normal operating range, results of the above techniques would change from a linear trend to non-linear behavior. For example, the phasic information for motor voltage (driving signal) and motor current (response signal) decreases as the flow decreases. The rate of change for the voltage-to-current phase increases when the pump flow is decreased past a low flow threshold, for example, about 3 L/min in one scenario. Thus, reviewing relative change of both power and phase shift helps to identify particular issues and situations when the flow estimator may be providing incorrect information. Moreover, using both phase relationship and average power in a controller, the controller can detect different levels of occlusion and additional friction (i.e. drag or impingement on rotor). For instance, occlusion results in a phase-power curve, whereas additional friction increases the average power. By combining the two measurements together one can generate a family of curves for identifying different levels of occlusion and different levels of friction (as discussed and illustrated later).

The same method can be applied using transfer function instead of phase change. The transfer function for voltage to current at specific frequencies will vary over a range of occlusion levels. The variation can be plotted with the average power at each scenario to produce an amplitude-power curve. Increasing the level of friction (i.e. drag or impingement on rotor) creates a family of these curves. Just like the plot with phasic information, the amplitude-power plot can be used to identify different levels of occlusion and different levels of friction.

As an illustration, a blood pump (such as, for example, a pump within a VAD) connected to the circulation system with an unobstructed connection to the heart and aorta can have a speed (response) signal that leads the voltage (driving) signal. In other words, the signals have a particular phase relationship (e.g., difference of phase angles of voltage and speed is negative). If an event occurs, such as an occlusion in the pump or stenosis at a conduit, the phase angle relationship changes according to the type of event. Alternately, viewing this illustration in terms of the relationship between current (response) signal and voltage (driving) signals, the phase angle of the current signal lags the phase angle of the voltage signal. Similarly, as the level of occlusion increases, the phase difference between the voltage (driving signal) and the current (response signal) decreases and the relationship becomes negative.

Figure 7:
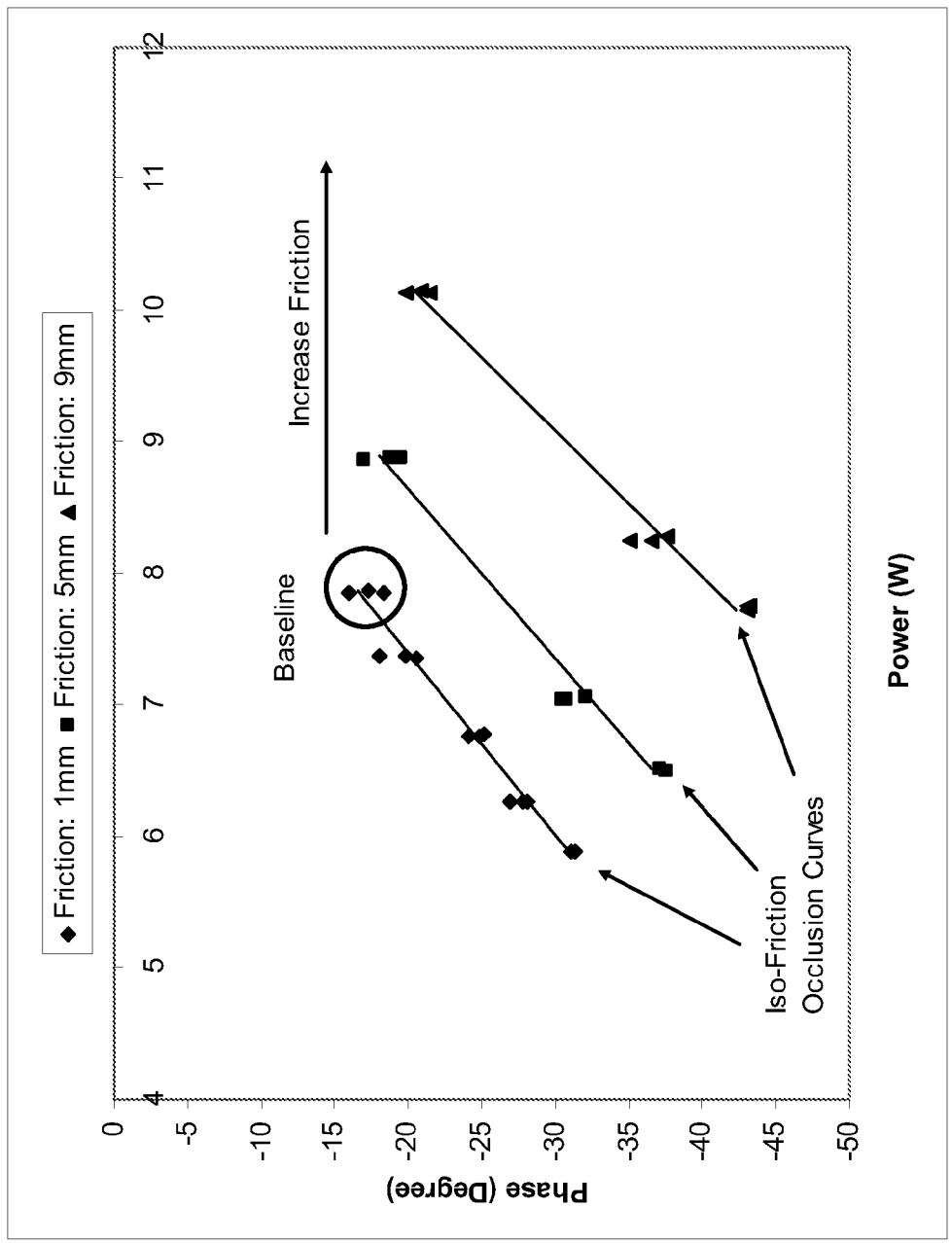
FIG. 7 is the mapping of different occlusion curves at different levels of friction; the variation in friction level results in creating family of occlusion curves in the phase-power plane.

In another example, current and voltage exhibit distinguishable responses to pump events and physiological conditions, similar to how power is affected by flow in the pump. The relationship between the relative phase angle change and relative power change can be approximated by a linear function. On the other hand, when the friction increases, only the power increases; there is negligible change to the phase. Plotting the phase angle difference and power levels for different levels of occlusion and friction, a family of phase-power curves for occlusion at different level of friction is created, as illustrated in FIG. 7 (and described earlier).

The second focus of the invention is to monitor occurrences of pump events and one or more other physiological conditions without the use of flow and pressure sensors or echocardiography. Pump events and physiological conditions include, but are not limited to, for example, a graft or conduit kink; drag on the pump or motor rotor, impeller, or bearing; a suction event; a pump flow status estimation; a change in peripheral vascular resistance manifesting itself as hypertension or hypotension; hypervolemia; tachycardia; arrhythmia, and tamponade.

In distinguishing different physiological conditions, the Fourier component (i.e., frequency of the peak amplitude) of a pump parameter (e.g., motor current) is sufficient in capturing the heart rate of the patient. Using this Fourier component, the analysis method can identify the patient's heart rate and the existence of tachycardia. The time-domain information of the pump's parameter (e.g., motor current) captures the intensity of the heart beat. By analyzing the variation in amplitude from cycle to cycle, this amplitude variation can identify the existence of arrhythmia. Furthermore, the time-frequency analysis which analyzes subset of the whole data length in a moving window provides result in amplitude, frequency, and time. It captures the change in the transient signal which can be used to identify events such as arrhythmia.

One advantage of the method is that it can differentiate effects of pump events in a fluid delivery system from effects of a patient's physiological conditions. In some embodiments of the present invention, the method allows not only the detection but also the quantification of pump events by analyzing certain parameters of the electric motor.

Under static conditions, it is difficult to differentiate the effects of pump events from the effects of a patient's physiological conditions. In particular, it is difficult to differentiate the effects of an occlusion at the pump from the effects of a change in peripheral vascular resistance in the patient's circulatory system. The occlusion and resistance change have similar effects on the static response of the system. Both change the electric motor's load, but it is difficult to determine how much of the change in load is attributable to the occlusion at the pump and how much of the change in load is attributable to the resistance change in the patient's circulatory system. As a result, it is difficult to determine whether there is an occlusion at the pump or resistance change in the patient's circulatory system from an increase in motor load under static conditions.

Under dynamic conditions, effects of pump events and physiological changes in the circulatory system on the behavior of a fluid delivery system can be identified. In other words, the pump impedance in a dynamic system is perceived differently depending on the different types of flow restriction. Therefore it is possible to differentiate the effects of pump events (e.g., occlusion) and physiological conditions (e.g., peripheral vascular resistance change) by analyzing the dynamic behavior of the system.

Distinguishing the effects of different types of occlusions can be accomplished, for example, by varying the value of one parameter of the system and then observing and analyzing the dynamic response of another parameter of the system. Although the varying or responding parameter can be any parameter of the system, such as any parameter of the pump or electric motor, it is preferred that the parameters selected can be easily controlled, measured and/or analyzed. For example, certain parameters of the electric motor, such as its voltage, current and speed, are readily available to the controller and can be easily controlled, measured or analyzed. In one embodiment, the voltage value of the electric motor is the parameter varied to induce a dynamic system response, and the response of at least one of the motor speed and current is analyzed to study system dynamic response. The voltage can be easily varied because the controller adjusts the voltage to control the system. In some cases, the input signal can be superimposed on an existing signal. For instance, a sinusoidal signal can be superimposed on an existing motor voltage signal that is used to control motor speed.

The input used to induce a dynamic system response can be intentionally-introduced, as discussed above, or naturally occurring. For example, changes in system load such as changes caused by the contracting heart take place naturally, and system responses to intentionally induced load changes can be used to analyze system dynamics.

Changes applied to a system parameter to induce a dynamic system response may include any one or combination of signal types. For example, the change can be a sinusoidal input of a certain frequency or any other periodic input such as a square wave input, or it can be a step input or a pulse input. In general, the change can be any signal that is not constant. With a periodic signal such as a sinusoidal signal, the time duration of the signal preferably is sufficiently long so that meaningful data can be collected for analysis. The time duration of the signal can be from 1 second to 30 seconds long, other time duration ranges are also possible. Although the frequency of a periodic signal can be of any suitable value, such as within 10 Hz, 30 Hz, 50 Hz or 100 Hz, it preferably is within the physiological frequency up to approximately 25 Hz. The input signal can be applied to the system periodically to monitor pump events (e.g., occlusion). An input signal can be applied to the system in regular or random intervals such as every hour, every day, every week, every month or every year. The length of the period between two applications can depend on how frequently or what event the pump is prone to experience. For instance, a more frequent application or monitoring may take place if a patient reduces intake of blood thinner to closely monitor if an occlusion begins to develop in the pump. This close monitoring may last for days or weeks until a physician can rule out a reduced intake of blood thinner will not lead to pump occlusion.

The various embodiments disclosed can employ a number of methods to analyze the dynamic response of the system for distinguishing and examining the effects of pump occlusion and circulatory system occlusion. For example, the dynamic behavior of the system can be analyzed in the time domain by examining the transient response of a system parameter to discern different effects of occlusions caused by pump or resistance increase of the circulatory system. In addition, the dynamic behavior of the system can be analyzed in the frequency domain by examining the frequency response of a system parameter. The frequency response of a system parameter may include one or both of the response's amplitude and phase at a single frequency or in a range of frequencies. The effects of pump and circulatory system resistance change result in relative changes in amplitude and/or phase in a frequency domain. For example, different degrees of resistance change can be represented or identified by relative changes in amplitude and/or phase in a frequency domain. Relationship between physiological resistance change and the dynamic response of a system parameter determine not only whether there is an occlusion at the pump but also the degree of occlusion at the pump. The degree of resistance change can be used to more accurately estimate the flow rate of a pump from the parameters of the electric motor. All of the above can be done in real time while the ventricular assist device is in operation to assist a patient's heart. In one embodiment, the control system has sufficient capacity to store the test data, conduct the analysis, and store the results of the analysis.

The following describes an example of how a system's frequency response can be used to detect and discriminate pump events (e.g., occlusion and friction) and circulatory system physiological conditions (e.g., peripheral vascular resistance change, hypertension, hypotension, tamponade, hypervolemia, and tachycardia etc.) The following tests were performed on a blood pump (e.g., ventricular assist device) similar to the one shown in FIG. 7. First, voltage of the electric motor was selected as an input parameter with a sinusoidal signal superimposed over the regular voltage signal. Then the responses of the motor's current and speed to the sinusoidal voltage input were recorded, and a Fast Fourier Transform was performed on the current and speed responses to obtain their frequency contents. The electric motor's current was measured at the control system and the speed was calculated from the back EMF without the use of any additional sensors. Various pump events (e.g., different degrees of pump occlusion) were artificially created at the pump, and the same test was performed for each pump event (e.g., different degree of pump occlusion.) The tests provide relationships between the different frequency contents of the motor's current and speed responses and the voltage input for different degrees of pump occlusion. In the tests, the degree of pump occlusion was measured in terms of the pump's flow rate for a given pump pressure differential. As the degree of pump occlusion increases, the pump's flow rate decreases.

Figure 2:
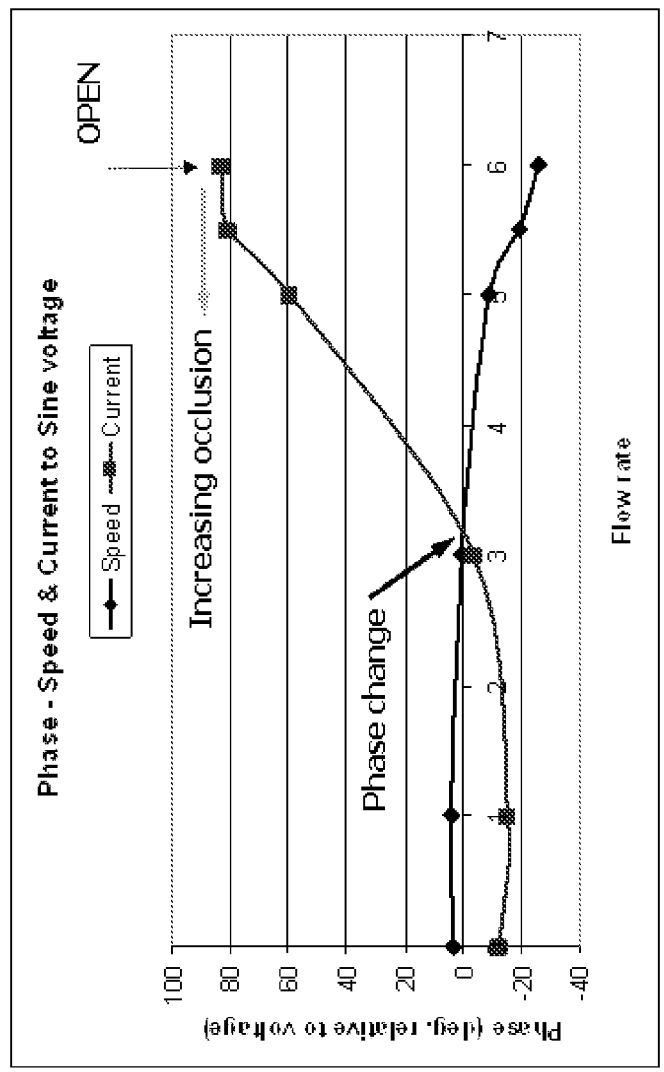
FIG. 2 illustrates the relationship between the phase difference between motor voltage and current, and pump occlusion as represented by pump flow rate; and the relationship between the phase difference between motor voltage and speed, and pump occlusion as represented by pump flow rate.
Figure 2:
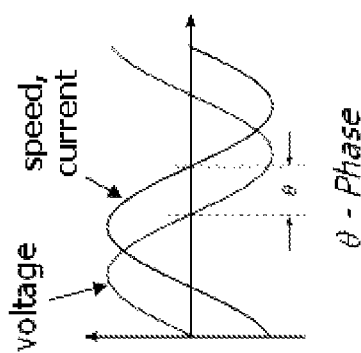
Figure 3:
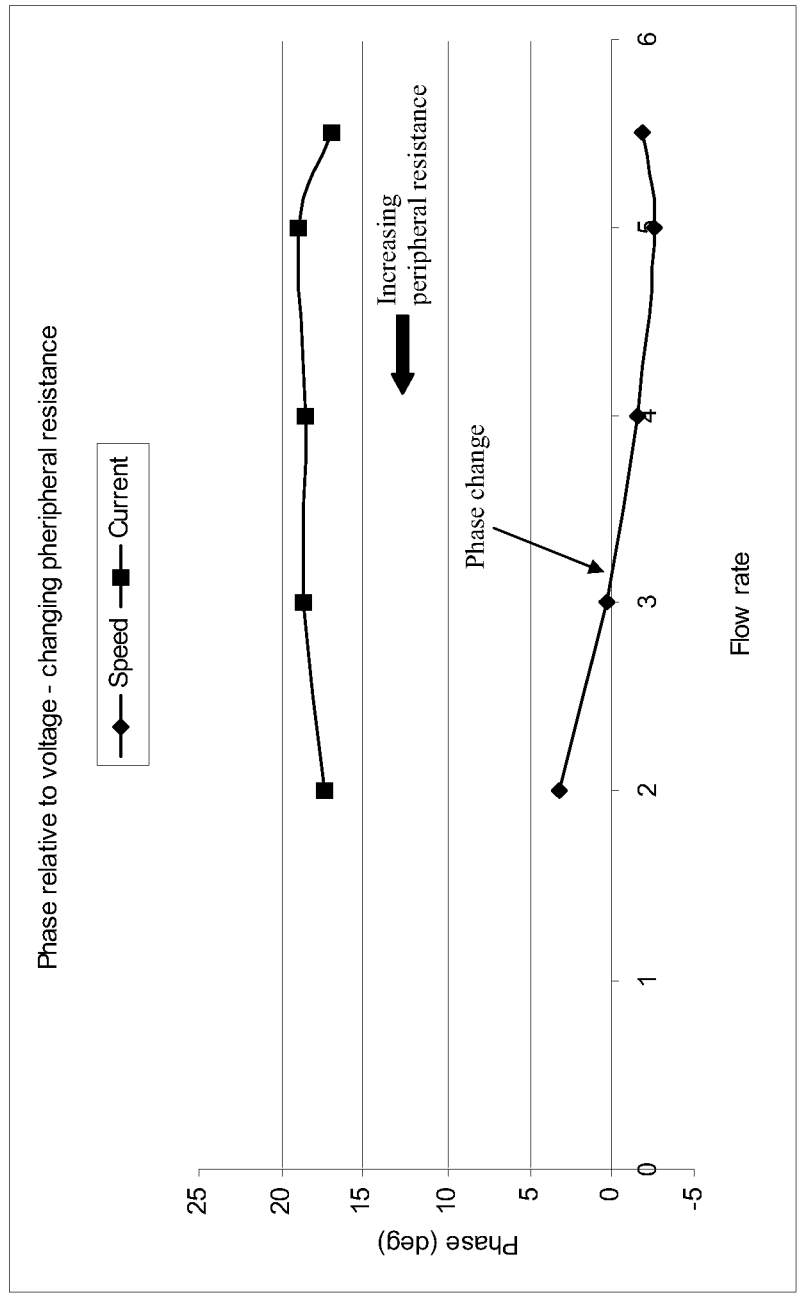
FIG. 3 illustrates the relationship between the phase difference between motor voltage and current, and peripheral occlusion as represented by pump flow rate; and the relationship between the phase difference between motor voltage and speed, and peripheral occlusion as represented by pump flow rate.

Some of the test results are represented as curves in FIGS. 2 and 3. In each of FIGS. 2 and 3, the vertical axis represents phase difference, and the horizontal axis represents flow rate. Since, as discussed above, the flow rate is used to measure the severity of pump occlusion, the horizontal axis actually represents the degree of pump occlusion. At the flow rate of six liters per minute there is no pump occlusion, while at the flow rate of zero the pump is completely occluded. The curve with square dots in FIG. 2 represents the relationship between pump occlusion and the phase difference between the motor voltage and motor current (i.e., the voltage's phase angle minus the current's phase angle) at the frequency of the sinusoidal voltage input. The curve with diamond dots in FIG. 2 represents the phase difference between pump occlusion and the motor voltage and motor speed (i.e., the voltage's phase angle minus the current's phase angle) at the frequency of the sinusoidal voltage input.

FIG. 3 is similar to FIG. 2, except that in FIG. 3 the horizontal axis represents peripheral vascular resistance change (in terms of flow rate), which is used to simulate physiological changes in a patient's circulatory system. The curve with square dots in FIG. 3 represents the relationship between peripheral vascular resistance change and phase difference between motor voltage and motor current at the frequency of the sinusoidal voltage input. The curve with diamond dots in FIG. 3 represents the phase difference between peripheral vascular resistance change and the motor voltage and motor speed at the frequency of the sinusoidal voltage input.

Figure 4:
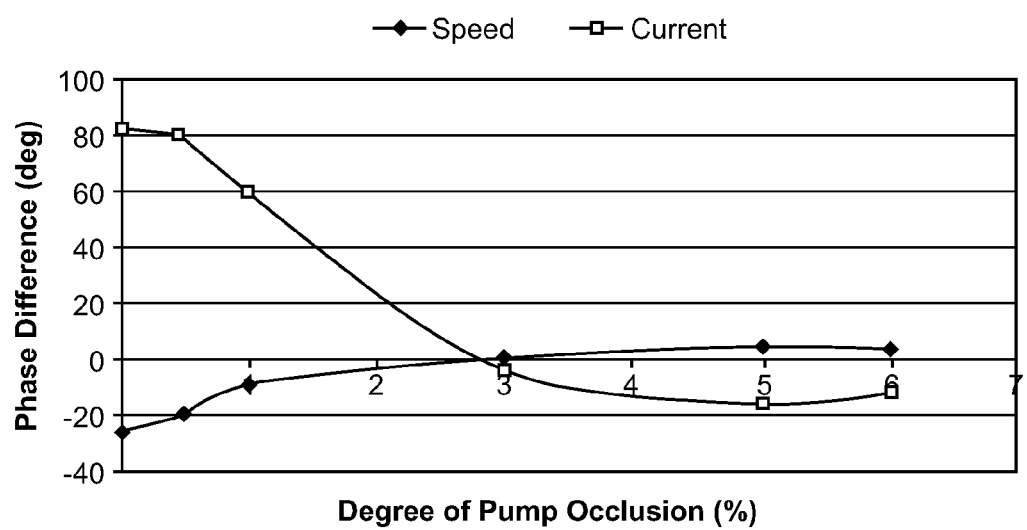
FIG. 4 illustrates the relationship between the phase difference between motor voltage and current, and pump occlusion; and the relationship between the phase difference between motor voltage and speed, and pump occlusion, where pump occlusion is directly represented by the horizontal axis.

FIGS. 2 and 3 can be reconfigured to more intuitively show the relationship between the phase differences and the degree of flow change due to pump occlusion or physiological resistance change. FIG. 4 shows the same replots the phasic information from FIG. 2 against degree of pump occlusion. Similarly, FIG. 5 shows the same phasic information as FIG. 3 but plotted against degree of peripheral vascular resistance change instead of flow.

FIG. 4 shows that pump occlusion has an effect on both the phase of motor current and the phase of motor speed. As pump occlusion increases, the phase difference between the motor voltage and motor current decreases from about 80° to about −17°, and the phase difference between the motor voltage and motor speed increases from about −25° to a small positive value.

Figure 5:
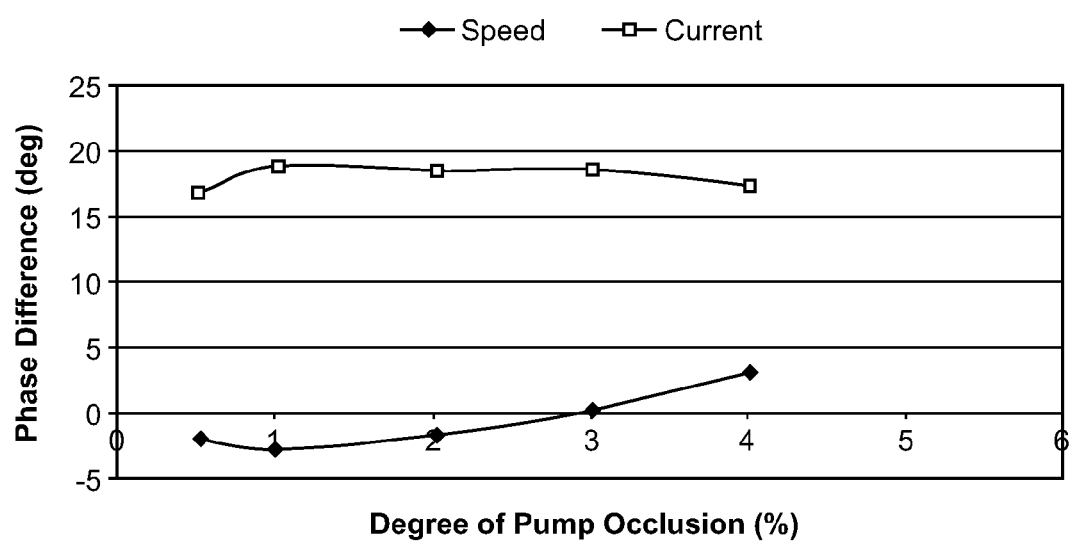
FIG. 5 illustrates the relationship between the phase difference between motor voltage and current, and peripheral occlusion; and the relationship between the phase difference between motor voltage and speed, and peripheral occlusion, where peripheral occlusion is directly represented by the horizontal axis.

FIG. 5 shows that peripheral vascular resistance change has a similar effect on the phase of motor speed. As peripheral vascular resistance increases, the phase difference between the motor voltage and motor speed increases from about a small negative value to a small positive value. The effect of peripheral vascular resistance on the phasic information between motor current and driving voltage is quite different from that of pump occlusion. The relative change in the phasic information for increase in peripheral vascular resistance is smaller than that from the pump occlusion. As peripheral vascular resistance increases, the phase difference between the motor voltage and the motor current remains within the narrow range of about 16° to about 19°.

As shown in FIGS. 4 and 5, the phase angle of the motor current varies significantly with pump occlusion while it does not vary much with peripheral vascular resistance change. Therefore, the phase angle of motor current can be used to determine not only whether there is an occlusion at the pump but also the degree of occlusion at the pump. For example, if the phase difference between the motor voltage and motor current changes from the historical value of 80° to 40°, the data would suggest that the flow rate reduces from 6 liters/minute to 4.5 liters/minute because of pump occlusion based on FIG. 2. In another example, if the phase difference between the motor voltage and motor current is negative, FIG. 2 would suggest that pump occlusion is quite severe.

Although the phase angle of motor speed can also be used to determine pump occlusion, it is more difficult in this example because pump occlusion and peripheral vascular resistance change have similar effects on the phase angle of motor speed. In other systems, it is possible that the phase angle, or amplitude, of motor speed is more suitable for determining the degree of pump occlusion than the phase angle of motor current. In general, either or both of the amplitude and phase angle of any signal may be used to determine pump occlusion.

In view of the above discussions, the control system 20 of the blood pump (e.g., VAD) 10 shown in FIG. 1 can be programmed to determine a degree of pump occlusion based on frequency domain information about a parameter of the electric motor. The degree of pump occlusion can be determined by real time calculations or by a table look up. In one embodiment, the parameter of the electric motor is the motor current. The control system 20 obtains the frequency domain information by supplying a variable voltage to the electric motor, sensing a response of the current of the electric motor to the variable voltage, and conducting frequency domain analysis of the response of the current of the electric motor to obtain the frequency domain information. The variable voltage includes the normal voltage signal used to control the blood pump (e.g., ventricular assist device) and a sinusoidal signal of a given frequency that is superimposed on the normal voltage signal. The frequency domain analysis can be performed using Fast Fourier Transform.

The frequency domain information can include a phase angle of the current of the electric motor at the given frequency or a phase difference that is a phase angle of the variable voltage at the given frequency minus the phase angle of the current of the electric motor at the given frequency. The frequency domain information can also include the amplitude of the current of the electric motor at given frequency or the transfer function of the variable signal (voltage or speed) and the current of the electric motor at given frequency, The control system can also be programmed to determine the degree of pump occlusion based on a predetermined relationship between a degree of pump occlusion and the phase difference between the variable voltage and the current of the electric motor. This relationship could be the current curve shown in FIG. 2. The predetermined relationship between a degree of pump occlusion and the phase difference may be stored in the memory of the control system.

Alternatively, the control system can be programmed to determine the degree of pump occlusion without the predetermined relationship. For example, the control system may be programmed to determine pump occlusion based on whether the phase difference between the variable voltage and the current of the electric motor is negative or positive. As shown in FIG. 2, a negative phase difference indicates a relatively severe pump occlusion, while a positive phase difference indicates a relatively small amount of pump occlusion.

Furthermore, the control system can be programmed to determine the degree of pump occlusion based on a historic record of the phase difference between the variable voltage and the current of the electric motor. For example, the control system may be programmed to determine the degree of pump occlusion based on how much the phase difference between the variable voltage and the current of the electric motor has decreased from its initial value. The relationship between the degree of pump occlusion and the decrease in phase difference can be determined from the current curve in FIG. 2.

Still, the control system can be programmed to estimate the flow rate of the pump using parameters of the electric motor, such as the speed of the motor and the power or current of the electric motor. U.S. Pat. No. 6,991,595, which is incorporated herein by reference, discloses a method for estimating the flow rate from the motor speed and motor power or from the motor speed and the current of the electric motor. The control system can be programmed to take into account the effects of pump occlusion on the calculation of pump flow rate. The effects of pump occlusion on the calculation of pump flow rate can be predetermined and then stored in the control system for reference. The control system can then determine the degree of pump occlusion and use the determined degree of pump occlusion to more accurately estimate pump flow rate based on the stored information.

Although the above describes certain blood pump or ventricular assist devices, the present invention is not limited to ventricular assist devices. In fact, the present invention can be used with any fluid delivery system. Additionally, the present invention is applicable to pumps of all types, including axial flow pump, centrifugal flow pump, displacement pump such as a gear pump or a reciprocating-type pump, and velocity pump such as a radial flow pump or a mixed flow pump, or even pumps with different modes of bearing suspension such as hydrodynamic bearing, magnetic bearing, and journal bearing. The present invention can be implemented in a continuous flow blood pump, such as axial or centrifugal flow pumps, that has a capability of inducing an artificial pulse.

Any of the above methods may be implemented using computer program languages such as, for example, ActiveX, Java, C, and the C++ language and utilize object oriented programming methodology. Any such resulting program, having computer-readable code, may be embodied or provided within one or more computer-readable storage media, thereby making a computer program product (i.e., an article of manufacture). The computer readable storage media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

Figure 6:
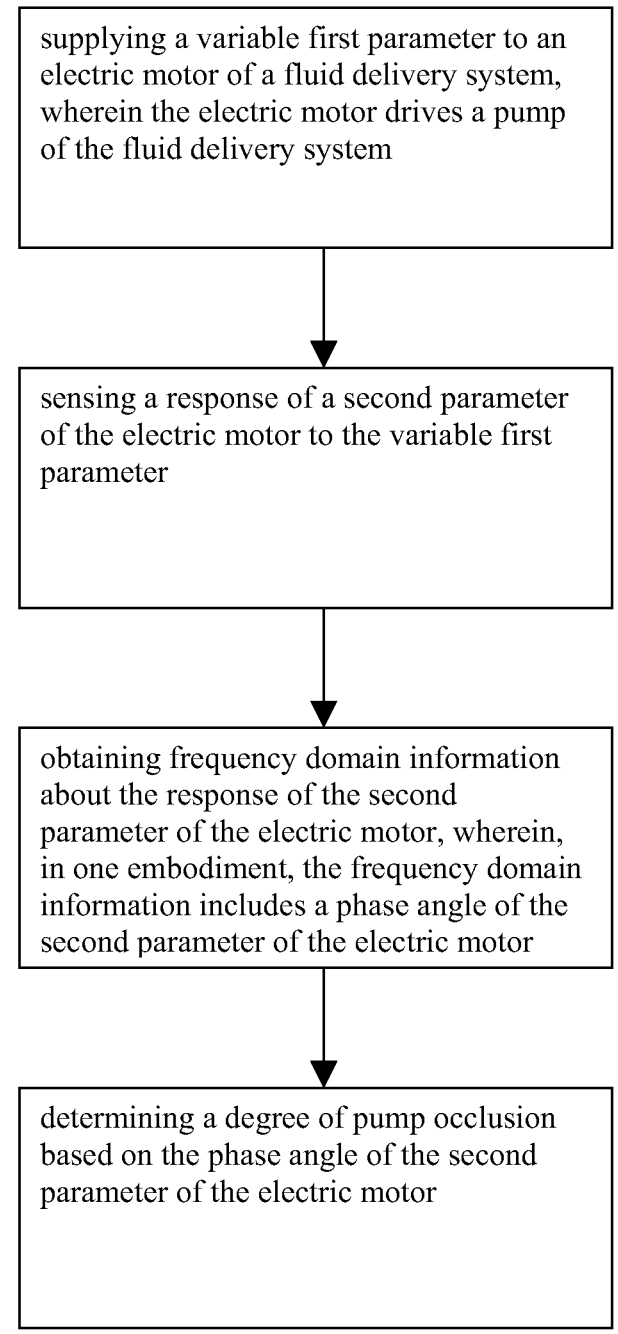
FIG. 6 is a flow chart showing computer instructions for carrying out the step of an exemplary method of the invention.

As shown in FIG. 6, the computer-readable code, which is embodied in the computer-readable storage media, computer program product or an article of manufacture, can have instructions for carrying out one or more steps of the following exemplary method:

Step 1: supplying a variable first parameter to an electric motor of a fluid delivery system, wherein the electric motor drives a pump of the fluid delivery system;

Step 2: sensing a response of a second parameter of the electric motor to the variable first parameter, for example in the form of voltage and current;

Step 3: obtaining frequency domain information about the response of the second parameter of the electric motor, wherein, in one embodiment, the frequency domain information includes a phase angle of the second parameter of the electric motor; and Step 4: determining a degree of pump occlusion based on the phase angle of the second parameter of the electric motor.

From the foregoing descriptions, it can be understood that a control system, for a blood pump driven by a motor, can be one that is programmed to generate and supply a driving signal (injected disturbance), that can be a variable voltage or speed command. The driving signal can be a non-steady speed or voltage waveforms. Optionally, the driving signal is not an artificial signal generated by the control system. For example, the driving signal can derived from the rhythm of a patient's heart The control system provides the driving signal to the electric motor in order to sense a response to the driving signal. The response signal can be a current or power of the electric motor or speed of the pump rotor. The control system is programmed to obtain frequency domain information about the response of the electric motor to the driving signal.

Analysis can be performed by the control system on various combinations of signal pairings, including without limitation: variable voltage and motor current, variable voltage and rotor speed, variable voltage and motor power, variable speed command and motor current, variable speed command and rotor speed, variable speed command and motor power, the motor current and the rotor speed, and the motor power and the rotor speed.

Analysis by the control system can include generating frequency domain information that includes the transfer function of the driving signal to response signal, the transfer function of one response signal to another response signal, and/or the transfer function any of the above listed signal pairings. The frequency domain information generated by the control system can include a transfer function that is the amplitude of one signal (e.g., motor current) at the given frequency divided by the amplitude of another signal (e.g., motor voltage) at the given frequency. The control system can be programmed to determine a degree of pump occlusion based on the transfer function between one signal and another signal at the given frequency.

Analysis by the control system can include generating frequency domain information that includes a phase angle of the response signal of the pump at a given frequency. The frequency domain information can include a phase difference that is a phase angle of the one signal (e.g., variable voltage) at the given frequency minus the phase angle of the another signal (e.g., motor current) at the given frequency. The control system can be programmed to determine a degree of pump occlusion based on the phase difference between one signal and another signal at the given frequency, and/or based on a predetermined relationship between a degree of pump occlusion and the phase difference between one signal and another signal, and/or based on whether the phase difference between one signal (e.g., the variable voltage) and another signal (e.g., the current of the electric motor) is negative or positive, and/or based on a historic record of the phase difference between one signal (i.e. the variable voltage) and another signal (i.e. the current of the electric motor), and/or based on how much the phase difference between one signal (e.g., the variable voltage) and another signal (e.g., the current of the electric motor) has decreased from its initial value. Said predetermined relationship is optionally stored in a memory of the control system or a remote memory accessed by the control system.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A system configured to control, monitor, or evaluate a blood pump driven by a motor, the system comprising:
a device programmed to analyze a driving signal with a non-steady component to the motor or the blood pump and a corresponding response signal received from the motor or to analyze two different response signals received from the motor resulting from the driving signal with the non-steady component, and to determine from the analysis whether the blood pump is in operation under either a pump event or a physiological event.

2. The system of claim 1, wherein the analysis includes generating information including one or a combination of frequency domain information, time domain information, and amplitude information, and comparing the information with data representative of one or both of the pump event and the physiological event.

3. The system of claim 1, further comprising a memory device storing data representative of one or both of the pump event and the physiological event, the memory device in communication with the device programmed to analyze.

4. The system of claim 1, wherein the pump event is one or a combination of events selected from the group consisting of occlusion, additional friction within the blood pump, thrombosis within the blood pump, kink in a graft or artificial conduit attached to the blood pump, increased drag on a rotor of the blood pump, increased drag on an impeller of the blood pump, and increased drag on an internal bearing of the blood pump.

5. The system of claim 1, wherein the physiological event is a change in peripheral vascular resistance.

6. The system of claim 1, wherein the physiological event is a condition selected from the group consisting of hypertension, hypotension, hypervolemia, tachycardia, arrhythmia, and tamponade.

7. The system of claim 1, wherein the device is programmed to match, in accordance with the analysis, an operating condition of the blood pump to a specific pump event from a plurality of pump events including occlusion, additional friction within the blood pump, thrombosis within the blood pump, kink in a graft or artificial conduit attached to the blood pump, increased drag on a rotor of the blood pump, increased drag on an impeller of the blood pump, increased drag on an internal bearing of the blood pump, and combinations thereof.

8. The system of claim 7, wherein the analysis includes phase-and-power analysis, amplitude-and-power analysis, or a combination thereof.

9. The system of claim 7, wherein the device is programmed to distinguish, in accordance with the analysis, the specific pump event from any one or plurality of physiological events including hypertension, hypotension, hypervolemia, tachycardia, arrhythmia, and tamponade.

10. The system of claim 9, wherein the analysis includes any one or a combination of phase-and-power analysis, amplitude-and-power analysis, peak amplitude frequency analysis, frequency-domain analysis, time-domain analysis, and time-frequency-domain analysis.

11. The system of claim 1, wherein the driving signal is based on the heart of a patient.

12. The system of claim 1, wherein the device is configured to supply the driving signal to the motor.

13. The system of claim 1, wherein the analysis includes generating frequency domain information that includes one or more of a transfer function component of the driving signal to the response signal, and a transfer function component of a first signal of the two different response signals to a second signal of the two different response signals, wherein each of the transfer function components includes phase information or amplitude information.

14. The system of claim 1, wherein the analysis includes generating frequency domain information that includes a transfer function of a pair of signals, the pair of signals selected from the group consisting of motor voltage and motor current, motor voltage and rotor speed, motor voltage and motor power, speed command signal and motor current, speed command signal and rotor speed, speed command signal and motor power, motor current and rotor speed, and motor power and rotor speed.

15. The system of claim 14, wherein the transfer function component is amplitude information of a first signal of the pair of signals at a selected frequency divided by amplitude information of a second signal of the pair of signals at the selected frequency.

16. The system of claim 14, wherein the device is programmed to determine a degree of pump occlusion based at least on the transfer function.

17. The system of claim 1, wherein the analysis includes generating frequency domain information that includes a phase angle of the response signal at a selected frequency.

18. The system of claim 17, wherein the frequency domain information includes a phase difference, the phase difference being a phase angle of the driving signal at the selected frequency minus the phase angle of the response signal at the given frequency.

19. The system of claim 18, wherein the device is programmed to determine a degree of pump occlusion based at least on the phase difference.

20. The system of claim 1 wherein the device is programmed to determine a degree of pump occlusion based at least on one or more of:
(a) a phase difference between the driving signal and the response signal at a selected frequency,
(b) a predetermined relationship between a degree of pump occlusion and a phase difference between the driving signal and the response signal,
(c) whether a phase difference between the driving signal and the response signal is negative or positive,
(d) a historic record of phase difference between the driving signal and the response signal, and
(e) a change in a phase difference between the driving signal and the response signal.

21. A pump system functioning as a ventricular assist device, the pump system comprising:
a blood pump driven by a motor; and
the device according to claim 1.

22. A method for controlling or monitoring a blood pump driven by a motor, the method comprising:
analyzing a driving signal with a non-steady component to the motor or the blood pump and a corresponding response signal received from the motor, or analyzing two different response signals received from the motor resulting from the driving signal with the non-steady component; and
determining from the analysis whether the blood pump is in operation under either a pump event or a physiological event.

23. The method of claim 22, wherein the analyzing step includes generating information including one or a combination of frequency domain information and time domain information, and comparing the information with data representative of one or both of the pump event and the physiological event.

24. The method of claim 22, wherein the pump event is a condition selected from the group consisting of occlusion, additional friction within the blood pump, thrombosis within the blood pump, kink in a graft or artificial conduit attached to the blood pump, increased drag on a rotor of the blood pump, increased drag on an impeller of the blood pump, increased drag on an internal bearing of the blood pump, and combinations thereof.

25. The method of claim 22, wherein the physiological event is a change in peripheral vascular resistance.

26. The method of claim 22, wherein the physiological event is a condition selected from the group consisting of hypertension, hypotension, hypervolemia, tachycardia, arrhythmia, and tamponade.

27. The method of claim 22, wherein the determining step includes matching an operating condition of the blood pump to a specific pump event from a plurality of pump events including occlusion, additional friction within the blood pump, thrombosis within the blood pump, kink in a graft or artificial conduit attached to the blood pump, increased drag on a rotor of the blood pump, increased drag on an impeller of the blood pump, increased drag on an internal bearing of the blood pump, and combinations thereof.

28. The method of claim 27, wherein the analysis step includes phase-and-power analysis, amplitude-and-power analysis, or a combination thereof.

29. The method of claim 27, wherein the determining step includes distinguishing the specific pump event from at least one physiological event including hypertension, hypotension, hypervolemia, tachycardia, arrhythmia, and tamponade.

30. The method of claim 29, wherein the analysis step includes any one or a combination of phase-and-power analysis, amplitude-and-power analysis, peak amplitude frequency analysis, frequency-domain analysis, time-domain analysis, and time-frequency-domain analysis.

* * * * *